(12) United States Patent  
Creaven et al.

(10) Patent No.: US 9,199,348 B2
(45) Date of Patent: Dec. 1, 2015

(54) PROSTHETIC VALVE CRIMPING

(71) Applicant: Medtronic, Inc., Minneapolis, MN (US)

(72) Inventors: Marian Creaven, Ballybrit (IE);
Alfonso D'Alessandro, San Francisco, CA (US); Niall Duffy, Ballybrit (IE); John Gallagher, Ballybrit (IE); Devin Gosal, Santa Rosa, CA (US); Scott Janis, Santa Rosa, CA (US); Karan Punga, Santa Rosa, CA (US); Glenn Stante, Santa Rosa, CA (US); Dick Yokota, Santa Rosa, CA (US); Misha Young, Cupertino, CA (US)

(73) Assignee: Medtronic, Inc., Minneapolis, MN (US)

( * ) Notice: Subject to any disclaimer, the term of this patent is extended or adjusted under 35 U.S.C. 154(b) by 321 days.

(21) Appl. No.: 13/777,164

(22) Filed: Feb. 26, 2013

(65) Prior Publication Data
US 2014/0144000 A1 May 29, 2014

Related U.S. Application Data

(60) Provisional application No. 61/730,248, filed on Nov. 27, 2012.

(51) Int. Cl.
*A61F 2/95* (2013.01)
*B23P 19/04* (2006.01)

(52) U.S. Cl.
CPC . *B23P 19/04* (2013.01); *A61F 2/95* (2013.01); *A61F 2002/9522* (2013.01); *Y10T 29/49908* (2015.01); *Y10T 29/53996* (2015.01)

(58) Field of Classification Search
CPC ... B23P 19/04; A61F 2/95; A61F 2002/9522; Y10T 29/53996; Y10T 29/49908

USPC .............................. 29/515, 514, 505, 283.5; 623/1.11–1.49, 2.11; 254/134.3 FT
See application file for complete search history.

(56) References Cited

U.S. PATENT DOCUMENTS

| 5,591,222 | A | * | 1/1997 | Susawa et al. ................ 606/195 |
| 5,893,852 | A | | 4/1999 | Morales |
| 5,992,000 | A | | 11/1999 | Humphrey et al. |
| 6,471,718 | B1 | | 10/2002 | Staehle et al. |
| 6,858,034 | B1 | * | 2/2005 | Hijlkema et al. ............. 606/108 |
| 8,518,106 | B2 | * | 8/2013 | Duffy et al. .................. 623/2.11 |
| 8,652,202 | B2 | * | 2/2014 | Alon et al. ................... 623/2.11 |
| 8,834,550 | B2 | * | 9/2014 | Leanna et al. ............... 623/1.11 |
| 2003/0225445 | A1 | * | 12/2003 | Derus et al. ................. 623/1.11 |

(Continued)

FOREIGN PATENT DOCUMENTS

| DE | 4235004 | 4/1993 |
| WO | WO2011/025970 | 3/2001 |

(Continued)

OTHER PUBLICATIONS

PCT/US2013/068558, PCT Search Report and Written Opinion, Mar. 18, 2014.

*Primary Examiner* — Jermie Cozart
*Assistant Examiner* — Bayan Salone

(57) ABSTRACT

A crimping tool includes a housing portion defining a funnel segment and a suture locking mechanism positioned to lock sutures therein. One or more sutures can be coupled with a prosthesis and secured to the suture locking mechanism. The suture locking mechanism can be operated to draw the prosthesis through the funnel segment.

22 Claims, 21 Drawing Sheets

(56) References Cited

U.S. PATENT DOCUMENTS

| | | | |
|---|---|---|---|
| 2004/0030381 A1* | 2/2004 | Shu | 623/2.11 |
| 2006/0020327 A1* | 1/2006 | Lashinski et al. | 623/1.25 |
| 2006/0020332 A1* | 1/2006 | Lashinski et al. | 623/2.11 |
| 2006/0025854 A1* | 2/2006 | Lashinski et al. | 623/1.25 |
| 2007/0239271 A1* | 10/2007 | Nguyen | 623/2.11 |
| 2007/0270931 A1* | 11/2007 | Leanna et al. | 623/1.11 |
| 2008/0071362 A1 | 3/2008 | Tuval et al. | |
| 2010/0049313 A1* | 2/2010 | Alon et al. | 623/2.11 |
| 2011/0060404 A1* | 3/2011 | Malewicz et al. | 623/2.11 |
| 2011/0208296 A1* | 8/2011 | Duffy et al. | 623/2.11 |
| 2011/0295216 A1 | 12/2011 | Miller | |
| 2012/0060348 A1* | 3/2012 | Chambers et al. | 29/505 |

FOREIGN PATENT DOCUMENTS

| | | |
|---|---|---|
| WO | WO01/35861 | 5/2001 |
| WO | WO2010096176 | 8/2010 |

\* cited by examiner

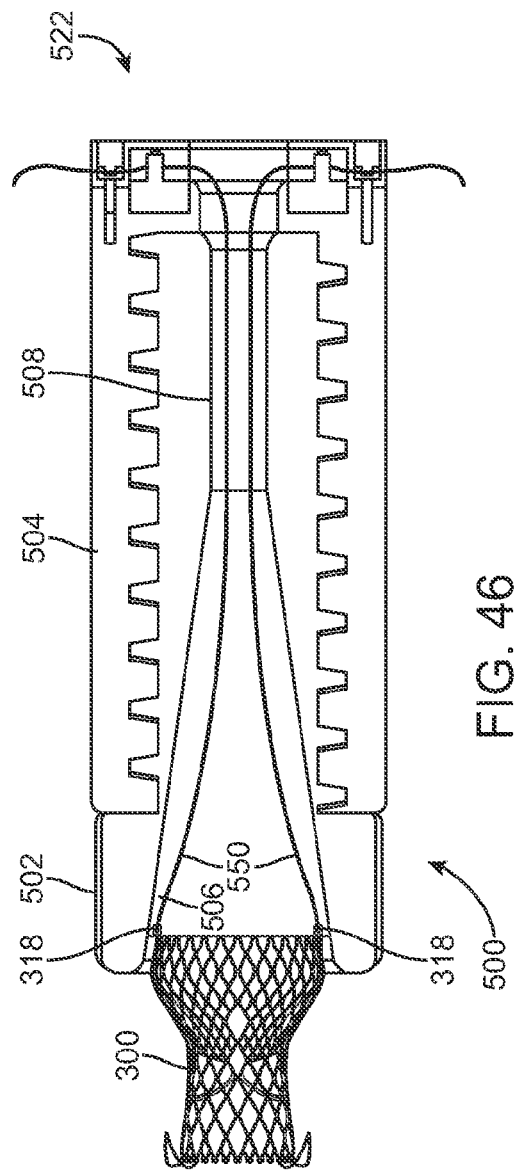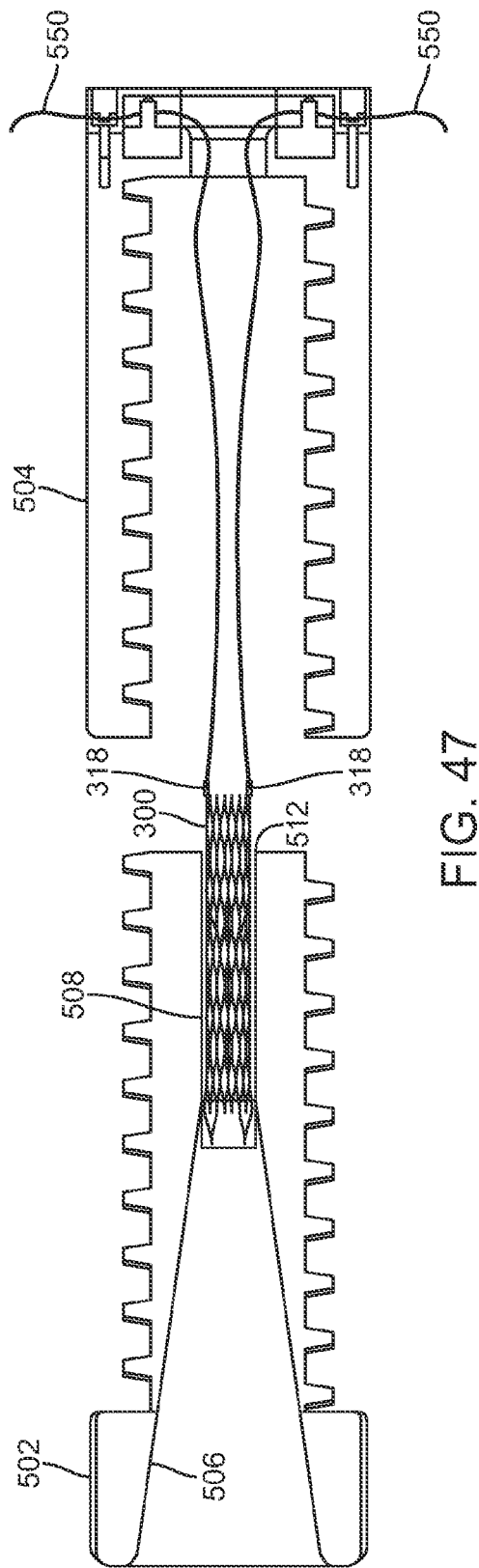

PROSTHETIC VALVE CRIMPING

CROSS-REFERENCE TO RELATED APPLICATION

This application claims priority under 35 U.S.C. §119(e) to U.S. Provisional Patent Application Ser. No. 61/730,248 filed on Nov. 27, 2012, and incorporated herein by reference.

BACKGROUND

Prostheses for implantation in blood vessels or other similar organs of the living body are, in general, well known in the medical art. For example, prosthetic vascular grafts formed of biocompatible materials (e.g., Dacron or expanded polytetrafluoroethylene (ePTFE) tubing) have been employed to replace or bypass damaged or occluded natural blood vessels.

A graft tube material supported by a framework is known as a stent-graft or endoluminal graft. In general, the use of stents and stent-grafts for treatment or isolation of vascular aneurysms and vessel walls which have been thinned or thickened by disease (endoluminal repair or exclusion) is well known.

Many stents and stent-grafts are "self-expanding", i.e., inserted into the vascular system in a compressed or contracted state, and permitted to expand upon removal of a restraint to an expanded or natural state. Self-expanding stents and stent-grafts typically employ a wire or tube frame configured (e.g., bent or cut) to provide an outward radial force and employ a suitable elastic material such as stainless steel or nitinol (nickel-titanium). Nitinol may additionally employ shape memory properties. A valve structure can be attached to the frame in some embodiments for use in replacement of a native valve.

The self-expanding stent or self-expanding stent-graft is typically configured in a tubular shape, sized to have a slightly greater diameter than the diameter of the blood vessel in which the stent or stent-graft is intended to be used. In general, rather than inserting it in a traumatic and invasive manner using open surgery, stents and stent-grafts are typically deployed through a less invasive intraluminal delivery, i.e., cutting through the skin to access a lumen or vasculature or percutaneously via successive dilatation, at a convenient (and less traumatic) entry point, and routing the compressed stent or stent-graft in a delivery system through the lumen to the site where the prosthesis is to be deployed.

Intraluminal deployment in one example is effected using a delivery catheter with coaxial inner tube, sometimes called an inner tube, and an outer tube, sometimes called the sheath, arranged for relative axial movement. The stent or stent-graft is compressed and disposed within the distal end of the sheath in front of the inner tube.

The catheter is then maneuvered, typically routed though a vessel (e.g., lumen), until the end of the catheter containing the stent or stent-graft is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent or stent-graft is gradually exposed from its distal end to its proximal end. The exposed portion of the stent or stent-graft radially expands so that at least a portion of the expanded portion is in substantially conforming surface contact with a portion of the interior of the blood vessel wall.

In order to compress the stent or stent-graft to the compressed state, crimping techniques are employed to transition the stent from the expanded state to the compressed state. Current crimping techniques involve several separate steps and various parts to load the stent to the delivery system. These techniques can be time consuming and prone to user error.

SUMMARY

Embodiments disclosed herein relate to crimping of a prosthesis. In one embodiment, a crimping tool includes a housing portion defining a funnel segment and a suture locking mechanism positioned to lock sutures therein. One or more sutures can be coupled with a prosthesis and secured to the suture locking mechanism. The suture locking mechanism can be operated to draw the prosthesis through the funnel segment.

A method for compressing a prosthesis from an expanded arrangement to a compressed arrangement includes threading a plurality of sutures through the prosthesis. The plurality of sutures are threaded through a funnel segment and a straight segment and the plurality of sutures are coupled to a suture locking mechanism. The suture locking mechanism is rotated to draw the prosthesis into the funnel segment and compress the prosthesis within the funnel segment.

BRIEF DESCRIPTION OF THE DRAWINGS

FIGS. 41-47 are successive views for compressing a prosthesis using the crimping tool of FIG. 40.

DETAILED DESCRIPTION

The present disclosure generally relates to crimping tools for compressing a stent frame from an expanded arrangement to a compressed arrangement. The stent can be positioned within the crimping tool and the tool is operated to compress the stent. While compressed, the stent can be coupled to a delivery system for delivering the stent to a deployment site. As used herein, the term "stent" is intended to encompass both stents and stent-grafts. For example, a stent may include a stent frame, a graft tube coupled to a frame, a prosthetic heart valve coupled to a frame, any combinations thereof, etc. The stents or stent grafts comprise frames that have a normal, expanded arrangement and a compressed arrangement for loading within the delivery system.

Some embodiments of the frames can be a series of wires or wire segments arranged such that they are capable of self-transitioning from the collapsed arrangement to the normal, radially expanded arrangement. In some constructions, a number of individual wires comprising the frame support structure can be formed of a metal or other material. These wires are arranged in such a way that the frame support structure allows for folding or compressing or crimping to the compressed arrangement in which the internal diameter is smaller than the internal diameter when in the natural, expanded arrangement. In the collapsed arrangement, such a frame support structure can be mounted onto a delivery system. The frame support structures are configured so that they can be changed to their natural, expanded arrangement when desired, such as by the relative movement of one or more sheaths relative to a length of the frame.

The wires of these frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This frame support structure can also be compressed and re-expanded multiple times without damaging the structure of the frame. In addition, the frame support structure of such an embodiment may be laser-cut from a single piece of material or may be assembled from a number of different components. For these types of frame structures, one example of a delivery system that can be used includes a catheter with a retractable sheath that covers the frame until it is to be deployed, at which point the sheath can be retracted to allow the frame to self-expand. In addition, a valve structure can be attached to the frame in some embodiments for use in replacing a native valve. Further details of such embodiments are discussed below.

Figure 1:
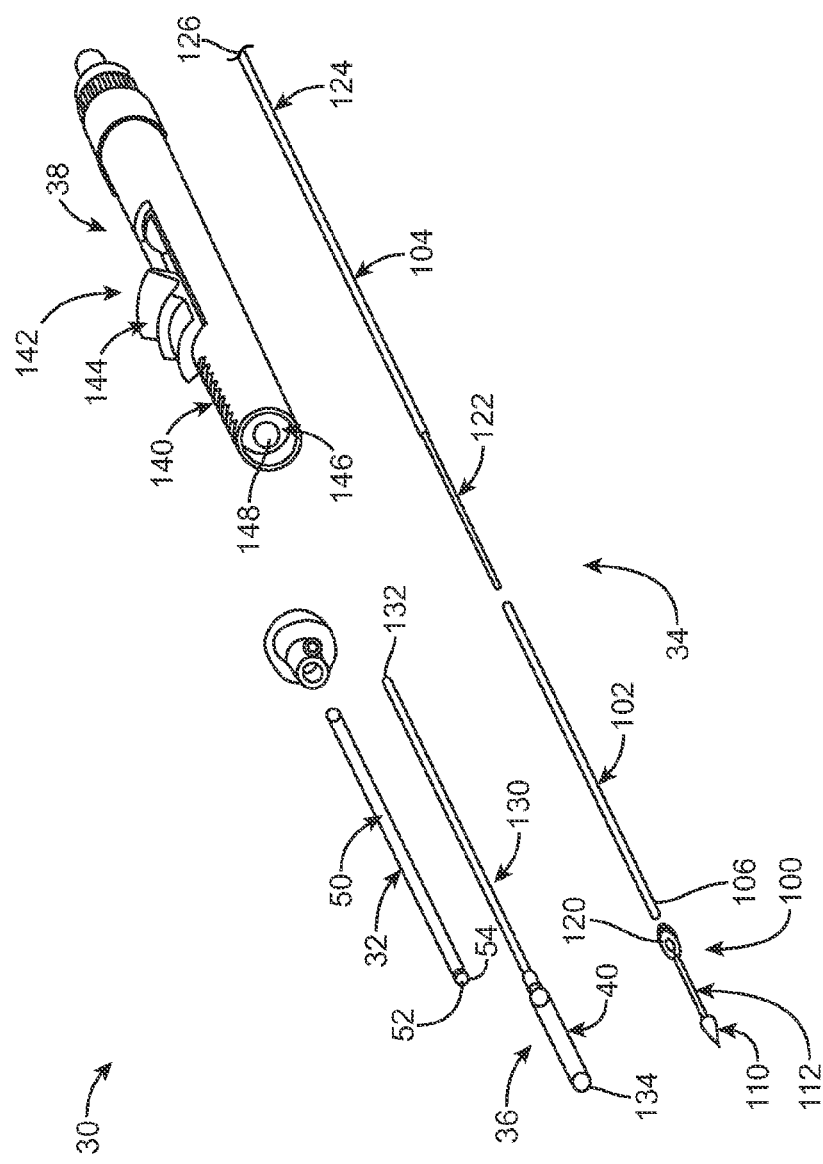
FIG. 1 is an isometric view of an exemplary delivery system.

With the above in mind, one embodiment of a stent delivery system 30 is shown in FIG. 1. The system 30 generally includes a stability layer 32, an inner shaft assembly 34, a delivery sheath assembly 36, and a handle 38. Details on the various components are provided below. In general terms, however, the delivery system 30 provides a loaded state in which a stent (not shown) is coupled to the inner shaft assembly 34 and compressively retained within a capsule 40 of the delivery sheath assembly 36. The delivery sheath assembly 36 can be manipulated to withdraw the capsule 40 proximally from the stent via operation of the handle 38, permitting the stent to self-expand and release from the inner shaft assembly 34. As a point of reference, various features of the components 32-38 reflected in FIG. 1 and described below can be modified or replaced with differing structures and/or mechanisms. Thus, the present disclosure is in no way limited to the stability layer 32, the inner shaft assembly 34, the delivery sheath assembly 36, the handle 38, etc., as shown and described below. More generally, delivery systems in accordance with the present disclosure provide features capable of compressively retaining a self-deploying stent (e.g., the capsule 40) and a mechanism capable of effectuating release or deployment of the stent.

The stability layer 32 illustratively includes a shaft 50, which forms a lumen 52 (referenced generally) sized to be slidably received over the inner shaft assembly 34, terminating at a distal end 54. The shaft 50 can take many forms and in general provides structural integrity to system 30, yet allowing sufficient flexibility to maneuver the capsule 40 to a target site (e.g., the aortic valve). To this end, shaft 50, in one embodiment, is formed of a polymeric material with an associated reinforcement layer. In other embodiments, the stability layer 32 can be eliminated.

The remaining components 34-38 of the delivery system 30 can assume a variety of forms appropriate for percutaneously delivering and deploying a self-expanding stent. For example, the inner shaft assembly 34 can have various constructions appropriate for supporting a stent within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stent within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slidably receive an auxiliary component such as a guide wire (not shown).

The retention member 100 can include a tip 110, a support tube 112, and an attachment mechanism 120. The tip 110 forms or defines a nose cone having a distally tapering outer surface adapted to promote atraumatic contact with bodily tissue. The tip 110 can have a diameter that is greater than, equal to or less than an outer diameter of a stent in the compressed arrangement when coupled to the delivery system 30. The tip 110 can be fixed or slidable relative to the support tube 112. The support tube 112 extends proximally from the tip 110 and is configured to internally support a compressed stent generally disposed thereover, and has a length and outer diameter corresponding with dimensional attributes of the selected stent. The attachment mechanism 120 is attached to the support tube 112 opposite the tip 110 (e.g., with an adhesive bond), and is configured to selectively capture a corresponding feature of the stent. A crimping tool can accommodate for differing sizes of tip 110 in positioning the stent for attachment to the attachment mechanism 120. The attachment mechanism 120 can assume various forms, and is generally located along an intermediate portion of the inner shaft assembly 34. In some constructions, the attachment mechanism 120 includes one or more fingers sized to be received within corresponding apertures formed by the stent frame (e.g., the stent frame can form wire loops at an end thereof that are received over respective ones of the fingers when compressed within the capsule 40).

The intermediate tube 102 is formed of a flexible polymer material (e.g., PEEK), and is sized to be slidably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube, at a proximal end 126. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the stent in the compressed arrangement. For example, the delivery shaft 130 can be a polymer tube embedded with a metal braiding, whereas the capsule 40 is a laser-cut metal tube. Alternatively, the capsule 40 and the delivery shaft 130 can have a more uniform construction (e.g., a continuous polymer tube). Regardless, the capsule 40 is constructed to compressively retain the stent at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms (i.e., controls) 142 (referenced generally). The housing 140 maintains the actuator mechanism(s) 142, with the handle 38 configured to facilitate sliding movement of the delivery sheath assembly 36 relative to the inner shaft assembly 34. The housing 140 can have any shape or size appropriate for convenient handling by a user. In one simplified construction, a first, deployment actuator mechanism includes a user interface or actuator (e.g., a deployment actuator) 144 slidably retained by the housing 140 and coupled to a delivery sheath connector body 146. The proximal end 132 of the delivery sheath assembly 36 is connected to the delivery sheath connector body 146. The inner shaft assembly 34, and in particular the proximal tube 104, is slidably received within a passage 148 (referenced generally) of the delivery sheath connector body 146, and is rigidly coupled to the housing 140 at proximal end 126.

As discussed in more detail below, crimping tools can be useful in compressing a prosthesis such as a stented prosthetic valve to a compressed arrangement for loading to delivery system 30. In particular, the crimping tools are configured to place compressive forces on the prosthesis and allow attachment mechanism 120 to be positioned for attachment of the prosthesis thereto. Once the prosthesis is attached to the attachment mechanism 120, capsule 40 can be distally advanced so as to retain the prosthesis in a delivery state.

Figure 2A:
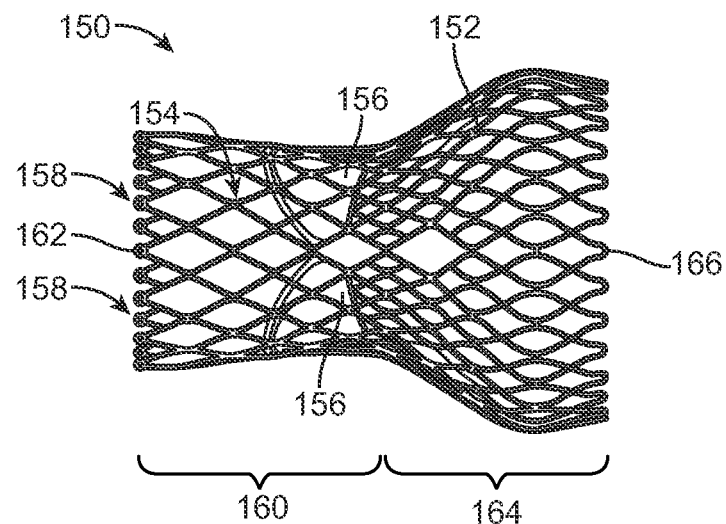
FIG. 2A is a side view of a stented prosthetic heart valve in an expanded arrangement.
Figure 2B:
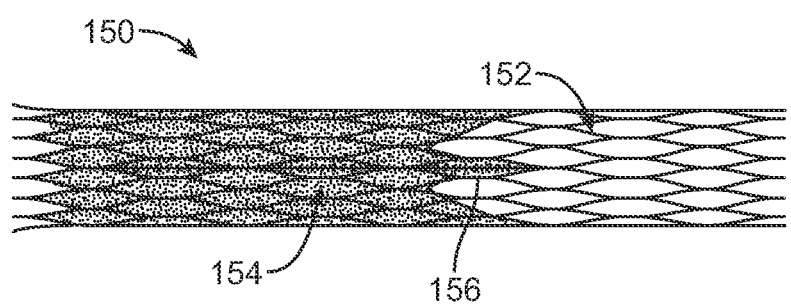
FIG. 2B is a side view of the stented prosthetic heart valve of FIG. 2A in a compressed arrangement.

With the above understanding in mind, one non-limiting example of a stented heart valve prosthesis (also referred to as a prosthetic heart valve) 150 useful with systems and methods of the present disclosure is illustrated in FIG. 2A. As a point of reference, the prosthetic heart valve 150 is shown in a normal or expanded arrangement in the view of FIG. 2A; FIG. 2B illustrates the prosthetic heart valve 150 in a compressed arrangement (e.g., when compressively retained within an outer catheter or sheath). The prosthetic heart valve 150 includes a stent or stent frame 152 and a valve structure 154. The stent frame 152 can assume any of the forms described above, and is generally constructed so as to be self-expandable from the compressed arrangement (FIG. 2B) to the normal, expanded arrangement (FIG. 2A). In other embodiments, the stent frame 152 is expandable to the expanded arrangement by a separate device (e.g., a balloon internally located within the stent frame 152). The valve structure 154 is assembled to the stent frame 152 and provides two or more (typically three) leaflets 156. The valve structure 154 can assume any of the forms described above, and can be assembled to the stent frame 152 in various manners, such as by sewing the valve structure 154 to one or more of the wire segments defined by the stent frame 152. A plurality of loops (or eyelets) 158 are provided on one end of the frame 152 for attachment to attachment mechanism 120 (FIG. 1).

With the but one acceptable construction of FIGS. 2A and 2B, the prosthetic heart valve 150 is configured for repairing an aortic valve and can be defined as including a first, inflow section 160 having an inflow end 162 and a second, outflow section 164 having an outflow end 166. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 2A and 2B, the valve structure 154 extends less than the entire length of the stent frame 152, but in other embodiments can extend along an entirety, or a near entirety, of a length of the stent frame 152. A wide variety of other constructions are also acceptable and within the scope of the present disclosure. For example, the stent frame 152 can have a more cylindrical shape in the normal, expanded arrangement. In addition, a variety of other structures can replace loops 158 for attachment to the attachment mechanism 120.

Figure 3:
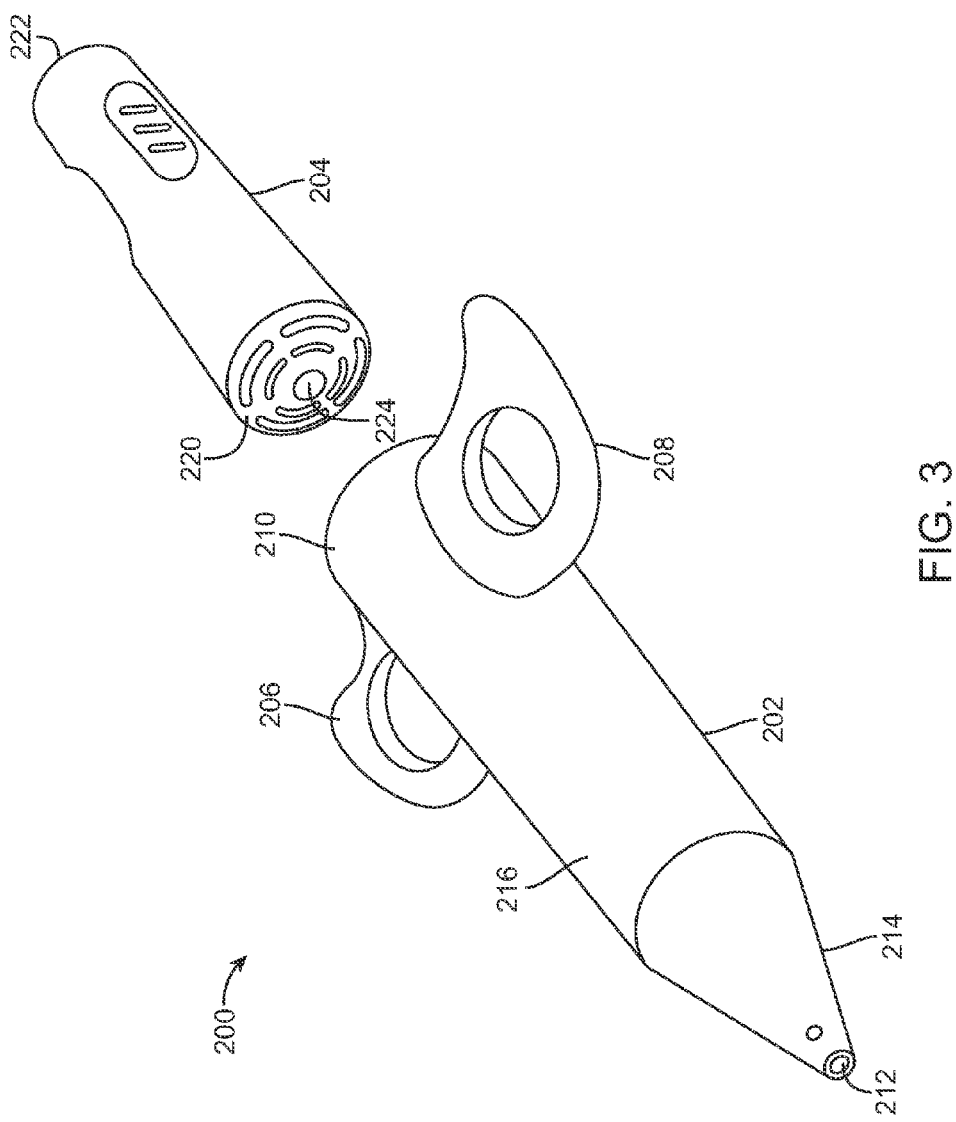
FIG. 3 is an isometric view of a crimping tool.
Figure 4:
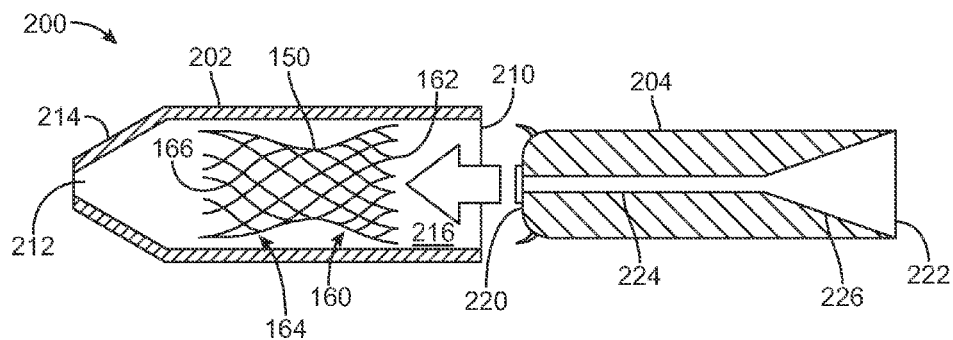
FIG. 4 is a sectional view of the crimping tool illustrated in FIG. 3.
Figure 28:
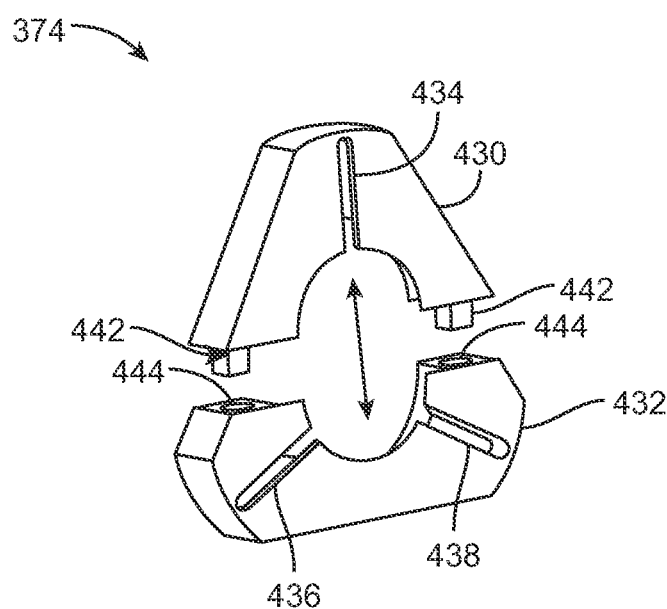

Given the above arrangements for valve 150, FIGS. 3 and 4 illustrate an exemplary embodiment of a crimping tool 200 for transitioning valve from an expanded arrangement (FIG. 2A) to a compressed arrangement (FIG. 28). Tool 200 includes a first housing portion 202 and a second housing portion 204 (embodied as a plunger) slidable with respect to the housing portion 202 and defining an outer diameter sized to fit within an inner diameter of first housing portion 202. Housing portion 202 includes first and second finger grips 206 and 208 for allowing a user to hold the housing portion 202 while inserting the plunger portion 204 into the housing portion 202. Housing portion 202 further includes a first open end 210 and a second open end 212 opposite the first end 210. The first end 210 defines an opening sized to receive the prosthesis 150 (FIG. 2A), whereas end 212 is sized to receive cone 110 of delivery system 30 (FIG. 1) for loading the prosthesis 150 thereto. The housing portion 202 also defines a funnel segment 214 and a straight segment 216 open to the first end 210. During use, a user inserts prosthesis 150 in end 210 and into segment 216.

Plunger 204 includes a first end 220 and a second end 222. First end 220 is open to a straight segment 224 whereas second end 222 is open to a funnel segment 226. As discussed below, end 220 of plunger 204 is configured to engage end 162 of valve 150 so as to advance the valve 150 toward the funnel segment 214 so that end 166 engages the funnel segment 214 and outflow section 164 is compressed due to advancement of plunger 204. Once outflow section 164 has been compressed, plunger 204 can be rotated such that end 222 engages end 162. Due to the shape of funnel segment 226, the inflow section 160 can be compressed by advancement of the plunger 204 into segment 216.

Figure 5:
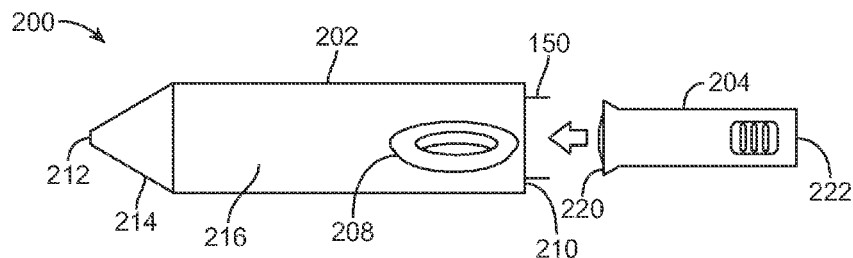
FIGS. 5-9 are views of successive steps for compressing a prosthesis with the crimping tool of FIG. 3.
Figure 6:
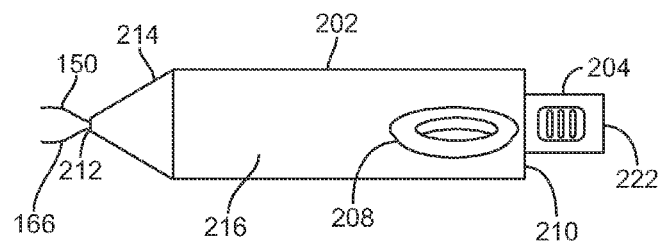
Figure 7:
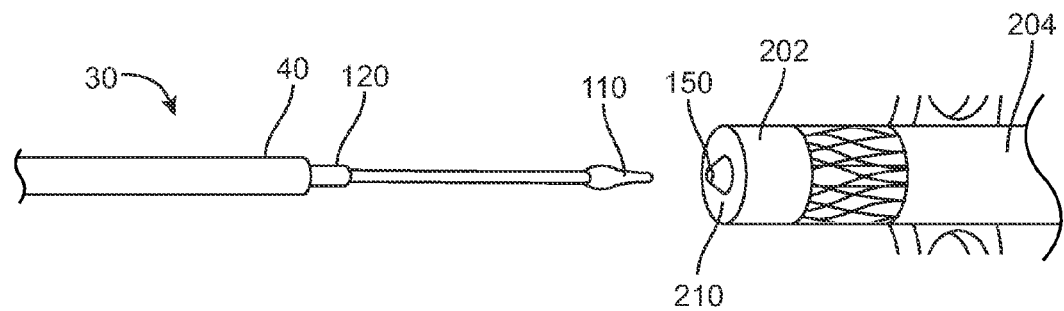
Figure 8:
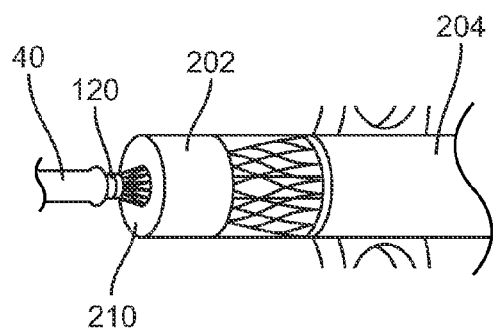
Figure 9:
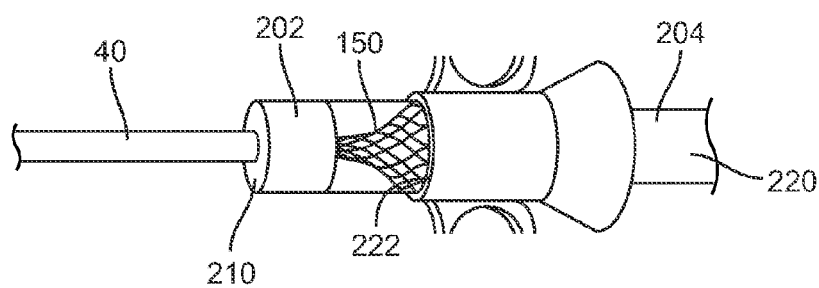
Figure 10:
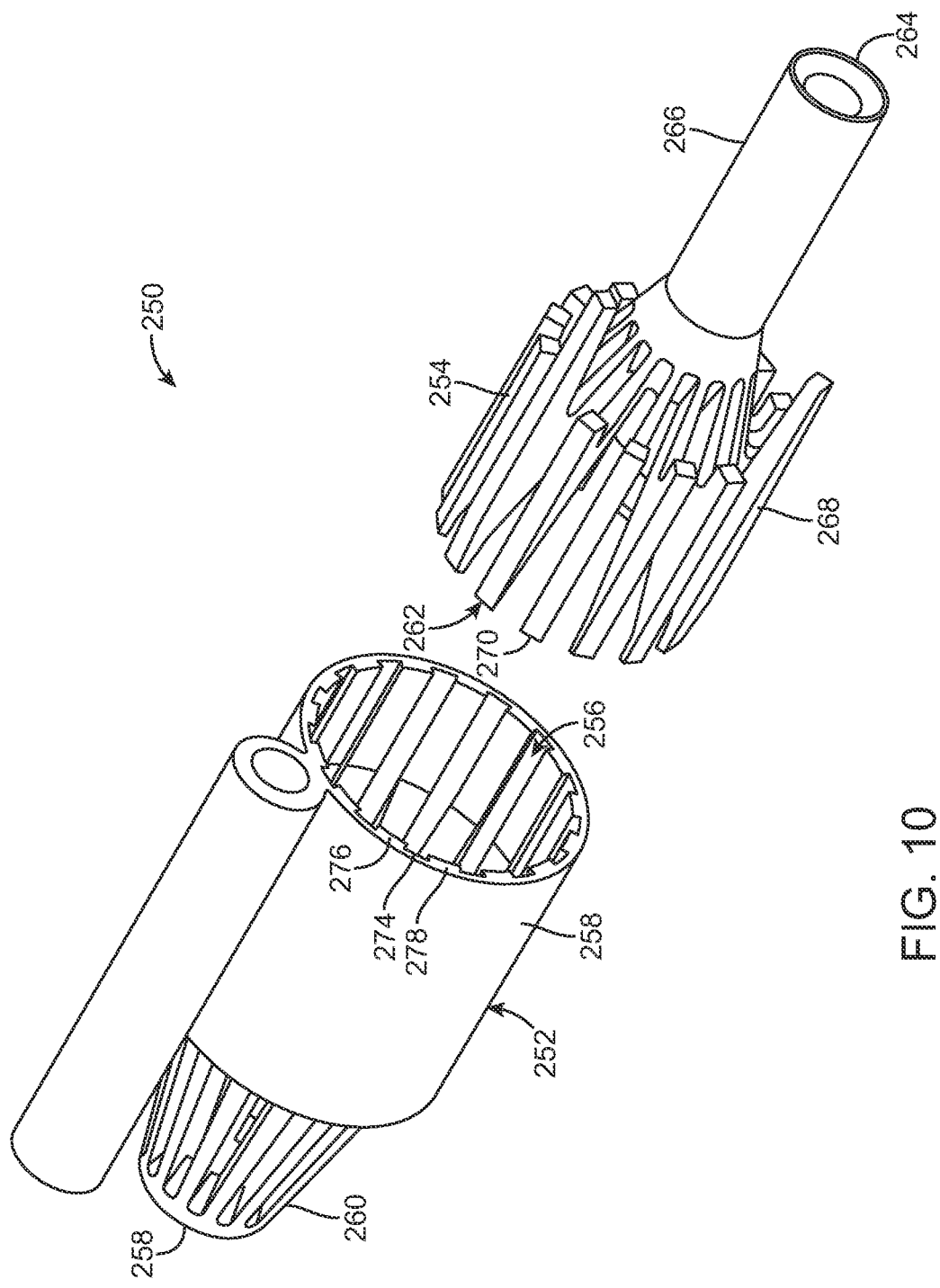
FIG. 10 is an isometric view of a crimping tool.

FIGS. 5-9 illustrate steps in loading a prosthetic heart valve 150 onto delivery system 30 of FIG. 1 using crimping tool 200. In FIG. 5, the valve 150 is loaded into the housing 202 and advanced into segment 216. In particular, end 220 of plunger 204 is inserted into end 210 of housing portion 202 and advanced along segment 216. In FIG. 6, advancement of the plunger 204 causes end 166 of the valve 150 to exit end 212 of the housing portion 202, exposing loops 158. As illustrated in FIG. 7, the tip 110 of delivery system 30 is advanced through the housing portion 202 in order to present coupling mechanism 120 of delivery device 30 for attachment of the loops 158 to the coupling mechanism 120. In FIG. 8, the coupling mechanism 120 is attached to the valve 150. Once the valve 150 has been attached to coupling mechanism 120, plunger 204 can be removed from the housing portion 202 and rotated to insert end 222 within end 210 of the housing portion 202 so as to compress inflow section 162. In FIG. 9, the capsule 40 is advanced to cover and retain the valve 150 in the compressed arrangement. Once the capsule 40 is advanced, crimping tool 200 can be removed such that delivery device 30 is ready for deployment of the valve 150.

FIGS. 10-16 illustrate an alternative crimping tool 250 comprising a first housing portion 252 and a second housing portion 254 slidable with respect to the first portion 252. Portion 252 includes a first open end 256 and a second open end 258 positioned opposite end 256. Portion 252 also includes a straight segment 258 and a funnel segment 260 for receiving and crimping a prosthesis. Similarly, portion 254 includes a first end 262 and a second end 264 opposite first end 262. Additionally, portion 254 defines a straight segment 266 and a funnel segment 268. Both of portions 252 and 254 include fingers or raised ridges that engage one another upon bringing the portions 252 and 254 together. For example, portion 254 includes a finger 270 configured to engage a recess 274 on portion 252 formed between corresponding fingers 276 and 278 formed in portion 252.

Figure 11:
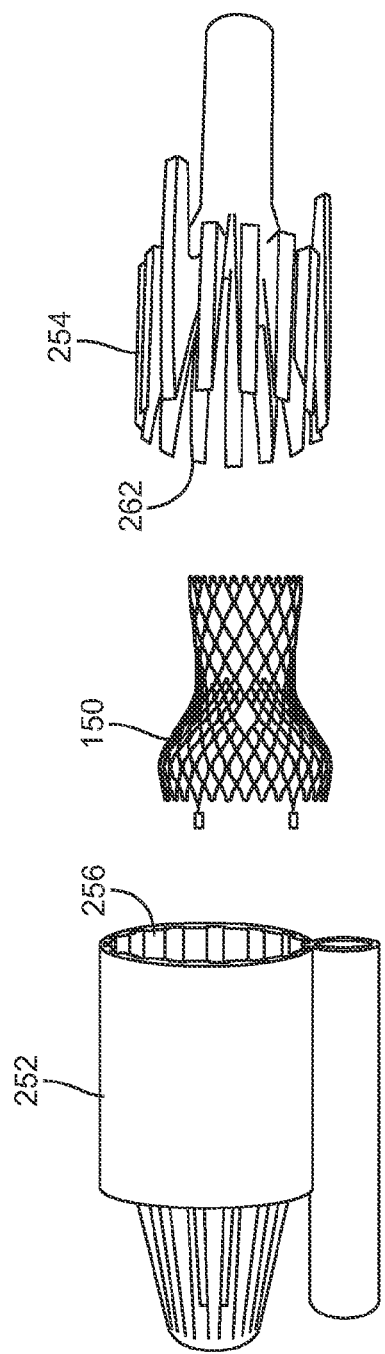
FIGS. 11-16 illustrate successive steps for compressing a prosthesis with the crimping tool of FIG. 10.
Figure 12:
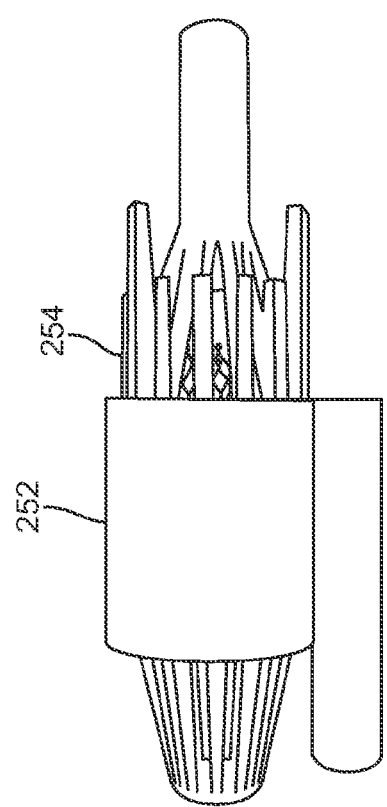
Figure 13:
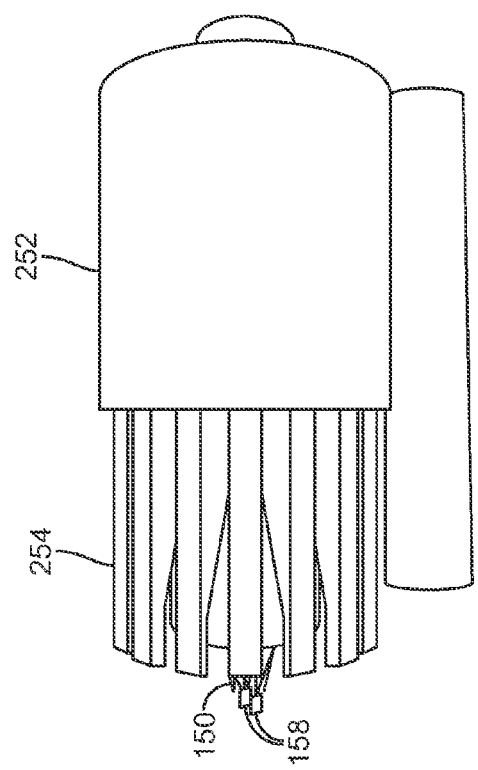
Figure 14:
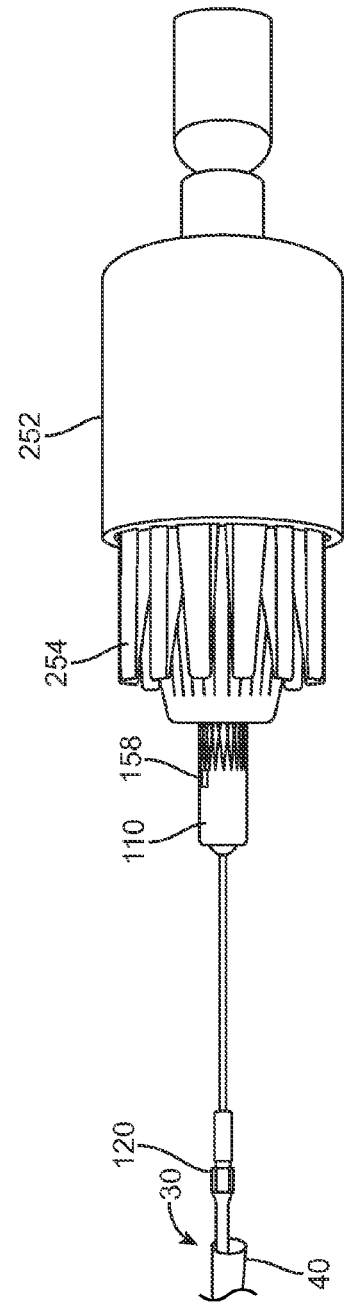
Figure 15:
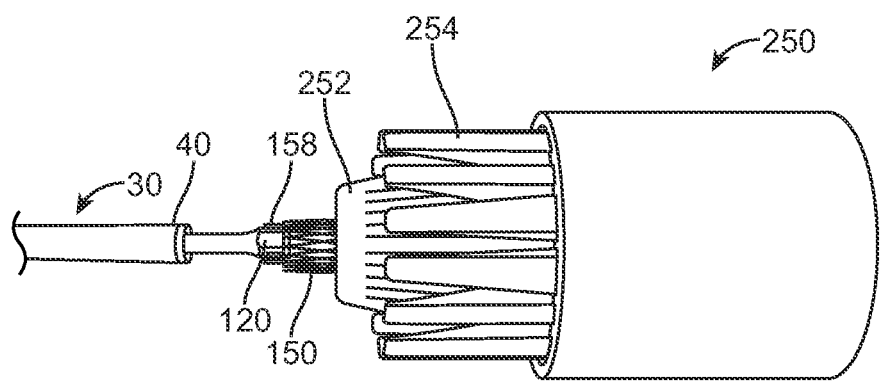
Figure 16:
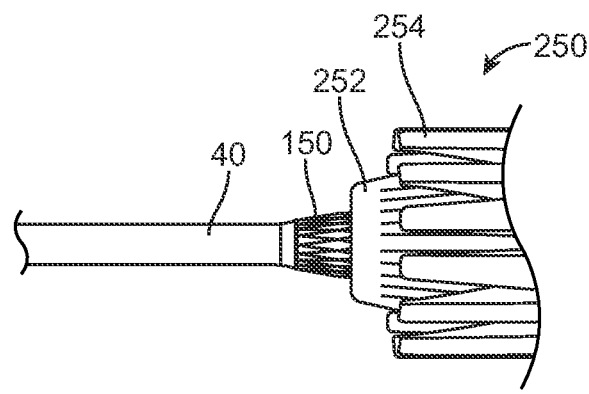

FIG. 11 illustrates portions 252 and 254 separated, wherein a valve prosthesis 150 can be inserted into end 256 and end 262 of portion 254. As shown in FIG. 12, portion 254 can be moved relative to portion 252 such that fingers of the respective portions interlock with one another such that portion 254 is nested within portion 252. Upon further advancement, as shown in FIG. 13, loops 158 of the valve 150 are exposed for attachment to delivery device 50. In FIG. 14, the cone tip 110 of delivery system 30 can be advanced into the crimping tool 250 such that the coupling mechanism 120 is adjacent loops 158 of the valve 150, as illustrated in FIG. 15. Once the valve 150 is attached to the coupling mechanism 120, the capsule 40 can be advanced to capture valve 150 as shown in FIG. 16.

Figure 17A:
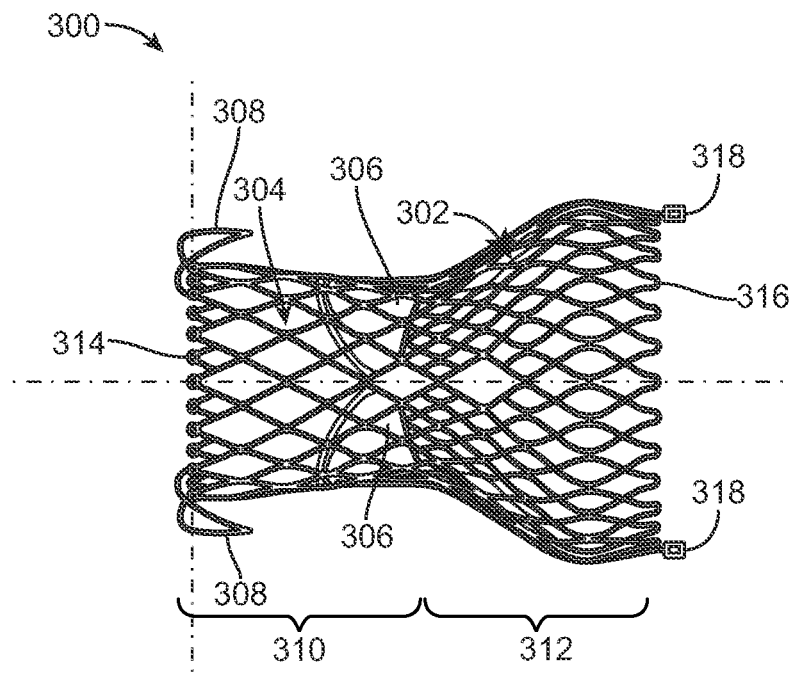
FIG. 17A is a side view of a stented prosthetic heart valve in an expanded arrangement.
Figure 17B:
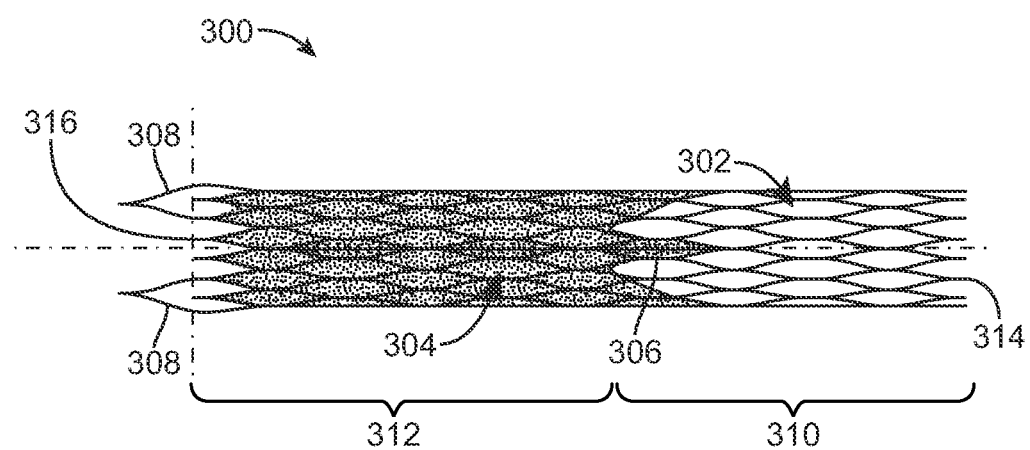
FIG. 17B is a side view of the stented prosthetic heart valve of FIG. 17A in a compressed arrangement.

In addition to prosthesis 150 discussed above, crimping tools can be configured to compress prostheses that include support arms coupled thereto as illustrated in FIGS. 17A and 17B. FIGS. 17A and 17B illustrate an exemplary mitral valve 300 that includes a stent frame 302 and a valve structure 304. The stent frame 302 can assume any of the forms described above, and is generally constructed so as to be self-expandable from the compressed arrangement (FIG. 17B) to the normal, expanded arrangement (FIG. 17A). In other embodiments, the stent frame 302 is expandable to the expanded arrangement by a separate device (e.g., a balloon internally located within the stent frame 302). The valve structure 304 is assembled to the stent frame 302 and provides two or more leaflets 306. The valve structure 304 can assume any of the forms described above, and can be assembled to the stent frame 302 in various manners, such as by sewing the valve structure 304 to one or more of the wire segments defined by the stent frame 302.

First and second opposed support arms 308 are positioned at an end of the stent frame 302 and configured to capture native leaflets of a mitral valve in the expanded arrangement of FIG. 17A. In the compressed arrangement of FIG. 17B, the support arms 308 are folded to extend in a direction away from the stent frame 302. As such, during crimping of valve 300, support arms 308 are folded away from the frame 302, referred to as prolapse of the support arms 308. Upon release from compressive forces retaining the valve in the compressed arrangement of FIG. 17B, support arms 308 will fold back upon the stent frame 302 to transition to the expanded arrangement. Given the components of the prosthetic heart valve 300, the valve can be defined to include an inflow section 310 (receiving fluid from an inflow end 314) and an outflow section 312 (forcing fluid out of an outflow end 316). One or more loops or eyelets 318 are attached to inflow and 314 and configured for attachment to attachment mechanism 120.

Figure 18:
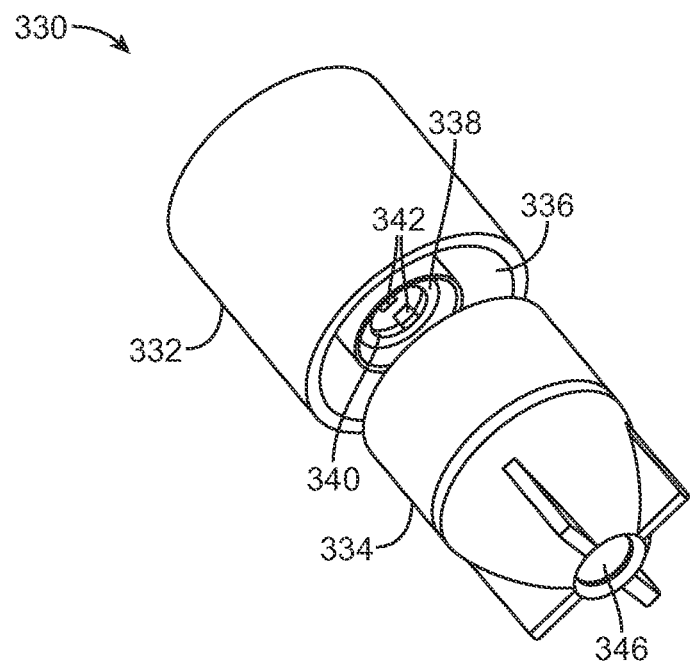
FIG. 18 is an isometric view of a crimping tool.
Figure 19:
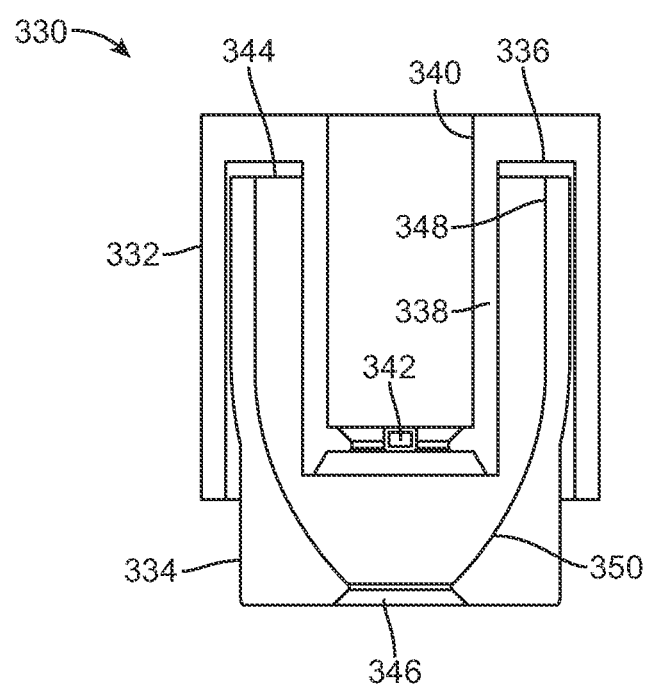
FIG. 19 is a sectional view of the crimping tool of FIG. 18.

FIGS. 18 and 19 illustrate an embodiment of a crimping tool 330 for crimping a mitral valve such as mitral valve 300 illustrated in FIGS. 17A and 17B. Tool 330 includes a first housing portion 332 and a second housing portion 334 slidable relative to the first portion 332. First portion 332 defines an interior annular cavity 336 configured to receive the second portion 334. Additionally, first portion 332 includes a projection 338 defining an internal aperture 340.

Projection 338 also includes tabs 342 configured to engage support arms 308 of valve 300 during crimping. Second portion 334 includes a first open end 344 and a second open end 346 opposite the first open end 344. The second portion 334 further includes a straight segment 348 and a funnel segment 350.

Figure 20:
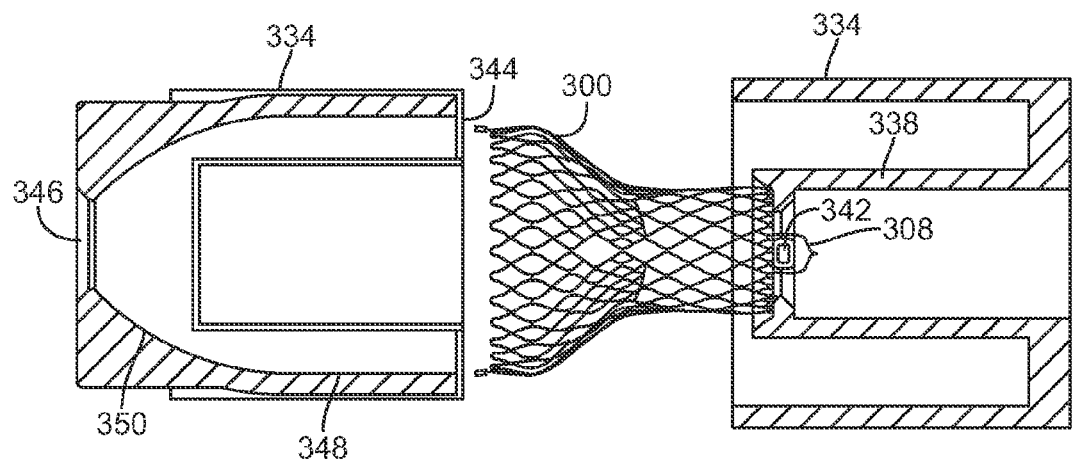
FIGS. 20-22 are successive views for compressing a prosthesis with the crimping tool of FIG. 18.
Figure 21:
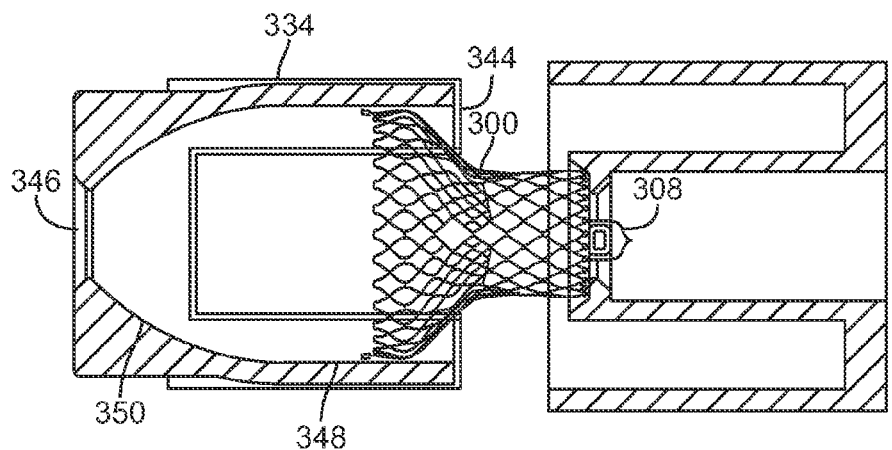
Figure 22:
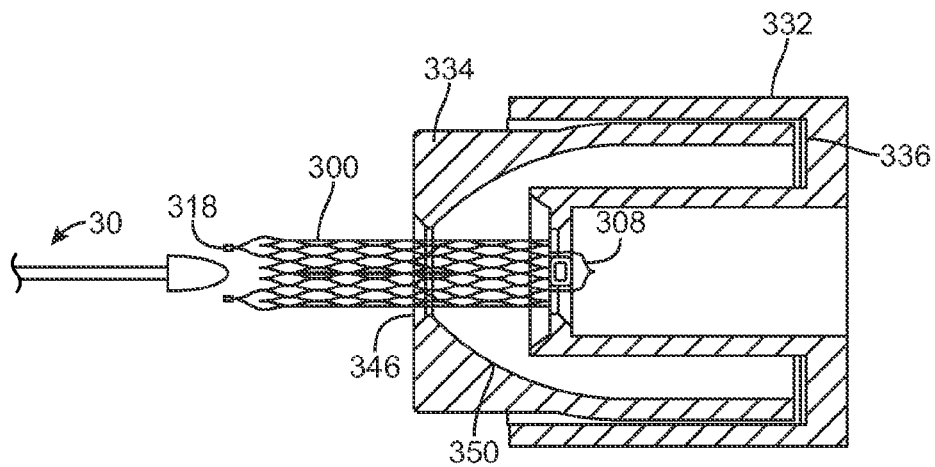

FIGS. 20-22 illustrate successive steps in using crimping tool 330 to crimp heart valve 300. In FIG. 20, valve 300 is attached to tabs 342 by folding back support arms 308 and coupling the support arms 308 to the tabs 342 on projection 338. In FIG. 21, portion 334 is slid toward portion 332, capturing valve 300 within the segment 348. In FIG. 22, portion 334 is fully seated within the annular cavity 336 of portion 332. Stent 300 is compressed by funnel segment 350 and exits the portion 334 through open end 346. The delivery system 30 can then be inserted through the valve 300 and open end 346 for coupling attachment mechanism 120 to loops 318. In an alternative embodiment, the delivery system 30 can be inserted into tool 330 and through valve 300 prior to crimping the valve 300. For example, delivery system 30 can be inserted into tool 330 in the step shown in FIG. 21.

Figure 23:
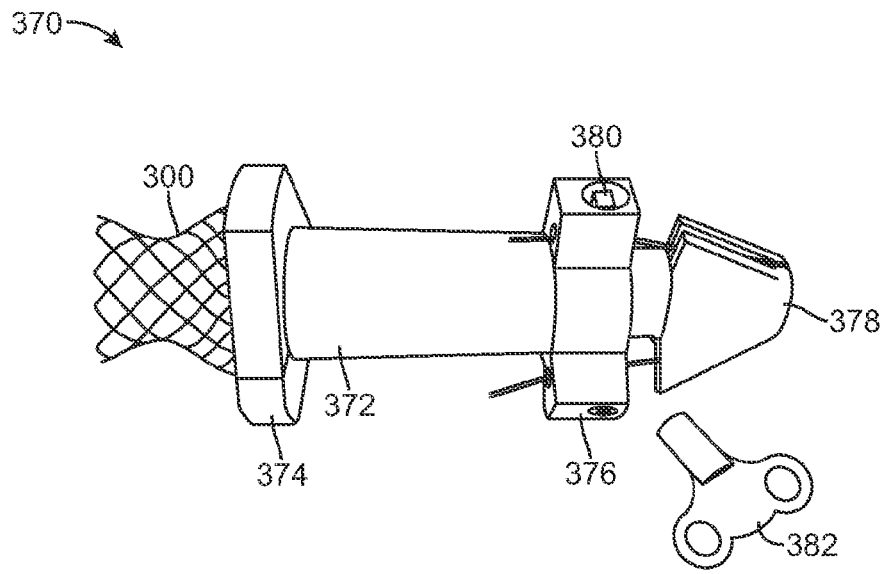
FIG. 23 is an isometric view of a crimping tool.
Figure 24:
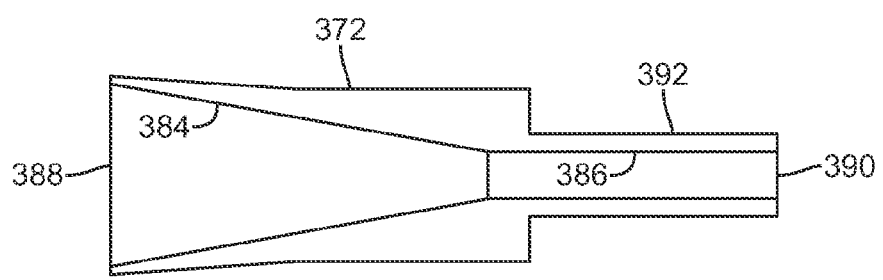
FIG. 24 is a sectional view of a housing portion of the crimping tool of FIG. 23.

FIG. 23 illustrates yet another crimping tool 370 that includes a housing portion 372, a spacer 374, a rotating knob 376 and a suture guide 378. The rotating knob 376 further includes a plurality of suture locking mechanisms 380 that are operated with a key 382. Although illustrated where mechanism 380 and key 382 are separate, each mechanism 380 can have a key 382 integral therewith or otherwise directly coupled thereto. FIG. 24 illustrates a sectional view of the housing portion 372, which includes an internal funnel segment 384 and an internal straight segment 386. Housing portion 372 further includes a first open end 388 and a second open end 390 opposite end 388. During crimping, the valve 300 is loaded into the open end 388 and advanced toward open end 390 to crimp the valve 300, as will be discussed below. The support arms 308 can prolapse during crimping using housing portion 372 such that the support arms pivot approximately 180° relative to stent frame 302 as otherwise illustrated in FIG. 17B. Portion 372 further includes a reduced front tip 392 for receiving the knob 376 and guide 378.

Figure 25:
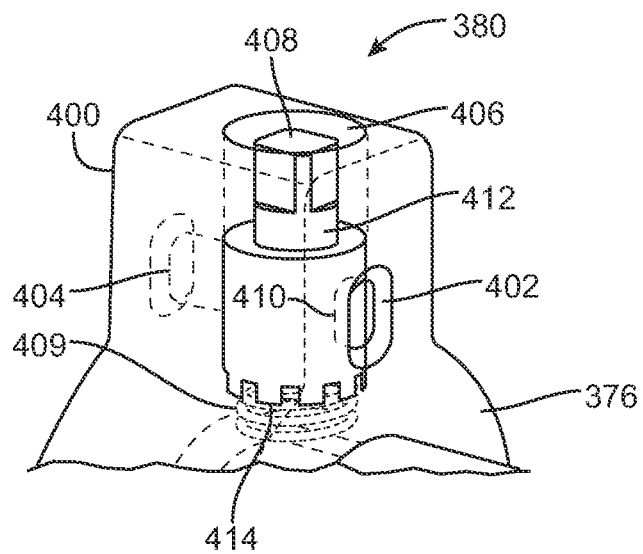
FIG. 25 is an isometric view of a suture locking mechanism of the crimping tool of FIG. 23.

FIG. 25 is a close up view of one suture locking mechanism 380 provided on knob 376. In one embodiment, three equally spaced locking mechanisms 380 are provided on the rotating knob 376, although any number of mechanisms can be used.

Mechanism 380 includes a raised projection 400 extending from the knob 376. Projection 400 includes a front aperture 402 and a rear aperture 404 leading to an internal bore 406. A pin 408 is positioned within the bore 406 and, in one embodiment, is spring loaded using a spring 409 to move relative to the bore 406. In particular, the spring 409 biases the pin 408 away from housing portion 372. The pin 408 includes a central aperture 410 and an upper portion 412 for interfacing with key 382. Additionally, the pin 408 includes a locking feature 414 (e.g., teeth) for locking pin 408 with respect to the projection 400. During use, the pin 408 is rotated such that aperture 410 aligns with apertures 402 and 404. A suture is then threaded through the aperture 402, bore 410 and aperture 404. Pin 408 can then be released so as to lock the suture with respect to projection 400. In particular, pin 408 is spring loaded such that, upon release of pin 408, aperture 410 moves out of alignment with apertures 402 and 404, causing the suture to lock within projection 400.

Figure 26:
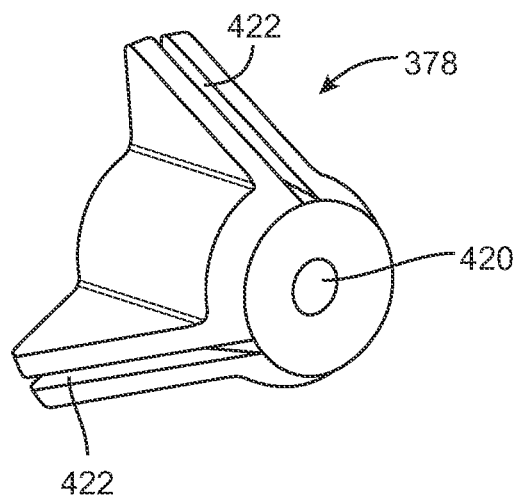
FIG. 26 is an isometric view of a suture guide of the crimping tool of FIG. 23.

FIG. 26 is an isometric view of guide 378 that includes an internal bore 420 and a plurality of channels 422 spaced apart around the guide 378. During use, sutures are threaded through bore 420 and positioned within channels 422 in order to secure the sutures while crimping. The channels 422 can be aligned with corresponding suture locking mechanisms 380 on knob 376 and, as such, a number of channels can be equal to a number of suture locking mechanisms 380.

Figure 27:
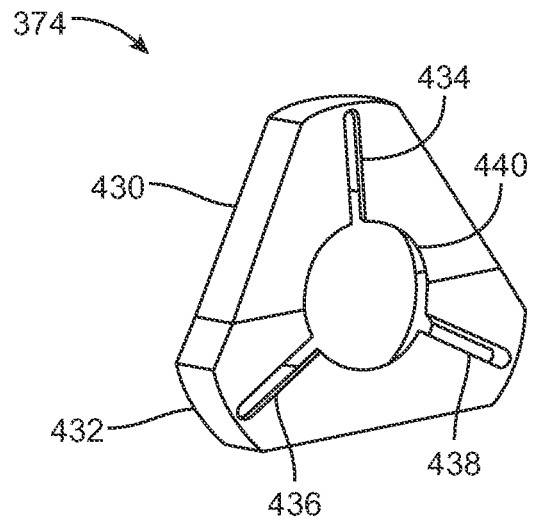
FIGS. 27 and 28 are isometric views of a spacer of the crimping tool of FIG. 23.

FIGS. 27 and 28 illustrate spacer 374, which includes an upper portion 430 and a lower portion 432. Upper portion 430 includes a channel 434 for receiving a suture and a lower portion 432 includes channels 436 and 438 for receiving loops 318. In particular, during tensioning of sutures, channels 434, 436 and 438 provide a guide for loops 318 to enter funnel segment 384. As such, the channels 434, 436 and 438 can be used such that sutures are tensioned equally. Additionally, the upper portion 430 and lower portion 432 combine to define an aperture 440 that surrounds the housing portion 372 and in particular tip 392. In one embodiment, spacer 374 is coupled to housing portion 372 so as to engage support arms 308 during crimping so as to assist in causing the support arms 308 to prolapse. As illustrated in FIG. 28, upper portion 430 includes a plurality of pins 442 for positioning within corresponding bores 444 in lower portion 432 so as to secure upper portion 430 to the lower portion 432.

Figure 29:
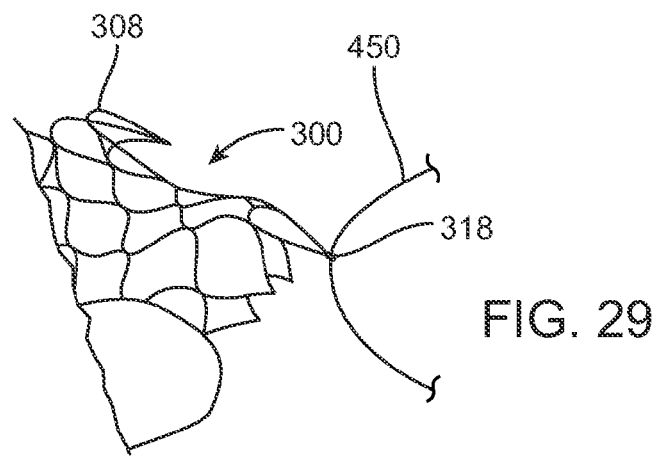
FIGS. 29-39 are successive views for compressing a prosthetic heart valve with the crimping tool of FIG. 23.
Figure 30:
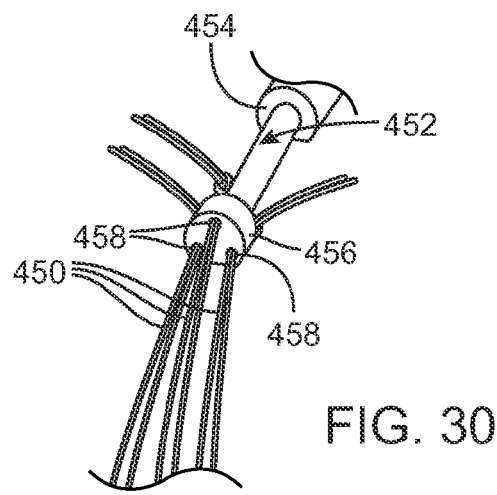

With the above description of crimping tool 370 in mind, FIGS. 29-38 illustrate successive steps for crimping mitral valve 300 utilizing crimping tool 370. As shown in FIG. 29, a suture 450 is threaded through each loop 318 on valve 300. Threading of other sutures 450 through loops 318 of valve 300 is repeated for each loop. In one embodiment, valve 300 includes three loops, although more or less loops can be used. In FIG. 30, each of the sutures 450 are attached to a suture loading tool 452. The suture loading tool 452 includes an elongated shaft 454 and an attachment end 456. The attachment end 456 includes a plurality of apertures 458 for receiving each of the sutures 450. The sutures 450 are tied with a knot on a side of the attachment mechanism 456 closest to elongated shaft 454.

Figure 31:
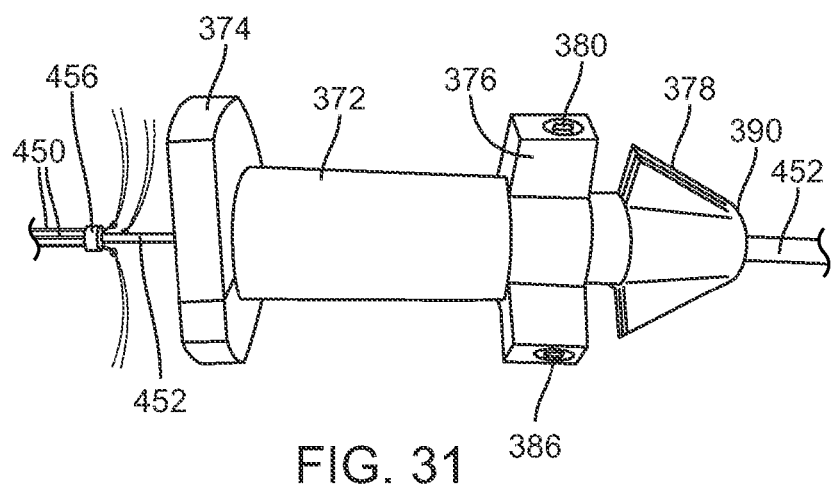
Figure 32:
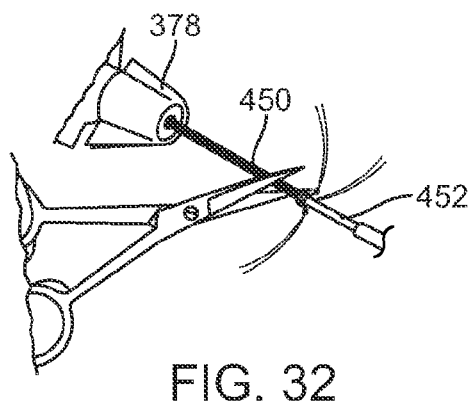
Figure 33:
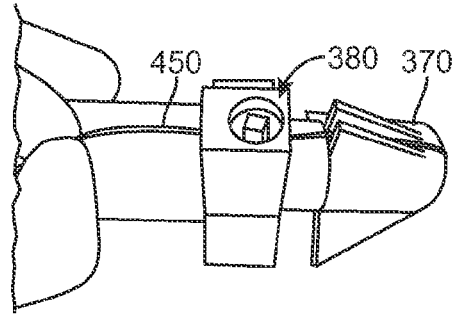
Figure 34:
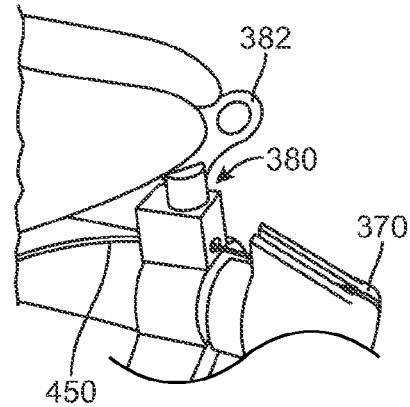
Figure 35:
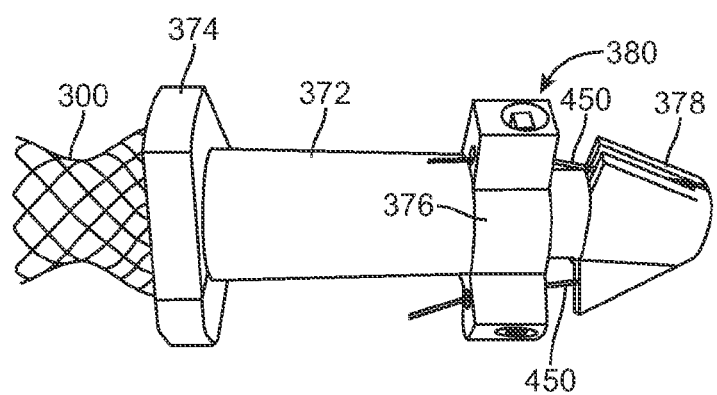

In FIG. 31, the suture loading tool 452 is pulled through the housing portion 372 and out end 390. As illustrated in FIGS. 32-34, each suture is cut at one end (FIG. 32), loaded within a corresponding suture locking mechanism 380 (FIG. 33), and tensioned using key 382 (FIG. 34). In FIG. 35, each of the sutures 450 are equally tensioned and each of the loops 318 are loaded within the housing portion 372 so as to engage funnel segment 384. Spacer 374 guides loops 318 into funnel segment 384 during tensioning.

Figure 36:
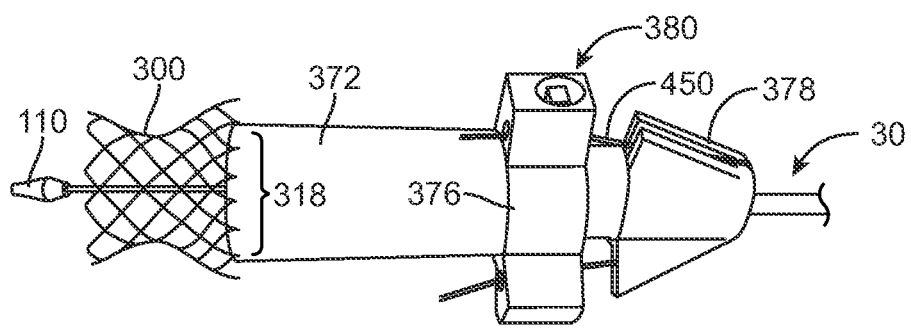
Figure 37:
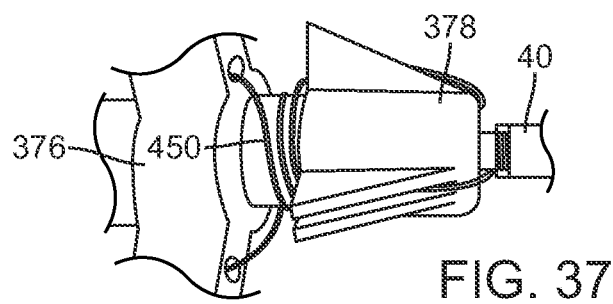
Figure 38:
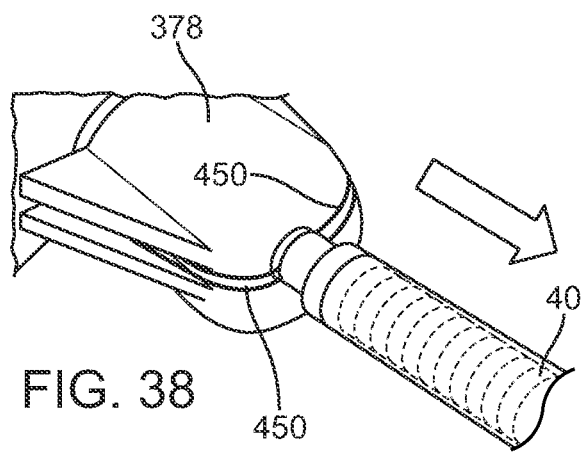
Figure 39:
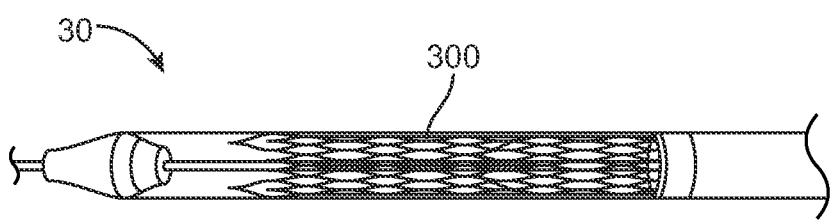

In FIG. 36, the spacer 374 can be removed from the funnel 372 and the delivery device 30 can be inserted through end 390 through housing portion 372 and out end 388 for loading the valve 300. In one embodiment, the crimping tool 370, valve 300 and delivery device 30 can further be immersed in ice cold saline. As shown in FIG. 37, the knob 376 can be rotated such that the plurality of sutures 450 pull the valve 300 toward end 390 such that the loops 318 are exposed for attachment to the delivery device 300. Sutures 450 wrap around housing portion 372 upon rotation of knob 376. Additionally, support arms 308 of the valve 300 engage the housing portion 372 so as to prolapse. In one embodiment, spacer 374 can be used to assist in prolapse of the support arms 308. In FIG. 38, the guide 378 can then be advanced over the delivery device 30. Further advancement of the delivery device 30 to crimp the valve 300 can then be provided and tool 370 be removed from device 30, as shown in FIG. 39.

Figure 40:
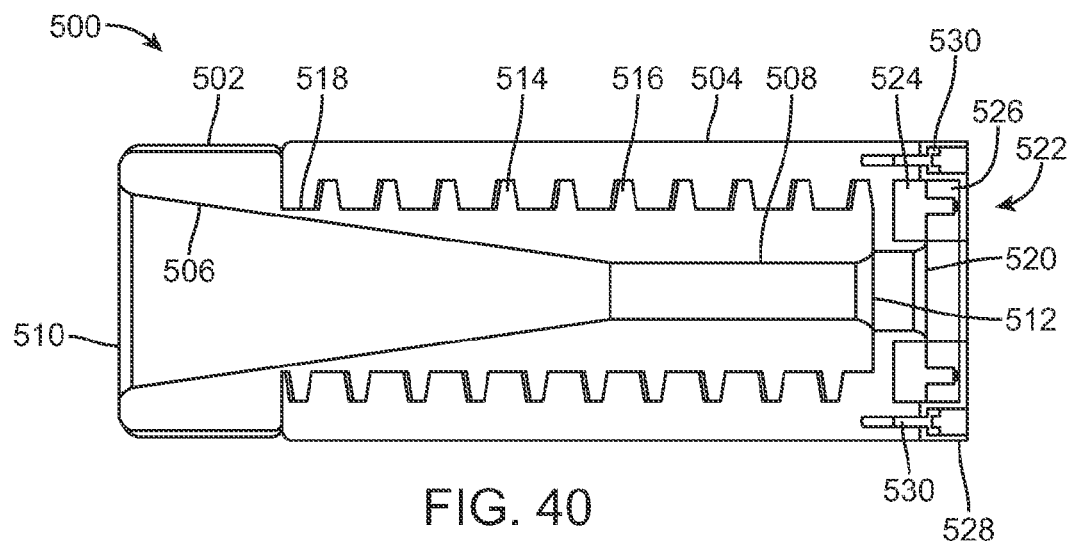
FIG. 40 is a sectional view of a crimping tool.

FIG. 40 illustrates an alternative embodiment of a crimping tool 500 that includes a first housing portion 502 and a second housing portion 504. Housing portion 502 includes an interior funnel segment 506 and a straight segment 508. Housing portion 502 further includes a first open end 510 coupled with the funnel segment 506 and a second open end 512 adjacent the straight segment 508. Cooperation of first housing portion 502 and second housing portion 504 is controlled by exterior threads 514 on housing portion 502 and interior threads 516 on housing portion 504. Housing portion 504 further includes a first opening 518 for receiving the housing portion 502 and a second opening 520 positioned at an opposite end of opening 518 to receive sutures threaded through crimping tool 500. Housing portion 504 further includes a suture locking mechanism 522 positioned proximate opening 520.

Suture locking mechanism 522 includes a rotating plate 524, a suture locking plate 526 and a lid 528 secured to the housing portion 504 with a plurality of fasteners 530. As discussed in FIGS. 41-47 below, a valve 300 can be loaded for crimping within crimping tool 500. In general, the valve 300 is loaded into funnel segment 506 and attached to suture locking mechanism 522 through one or more sutures. The housing portion 502 can then be advanced away from housing portion 504 by rotating the portion 502 relative to portion 504 such that valve 300 is urged through straight segment 508.

Figure 41:
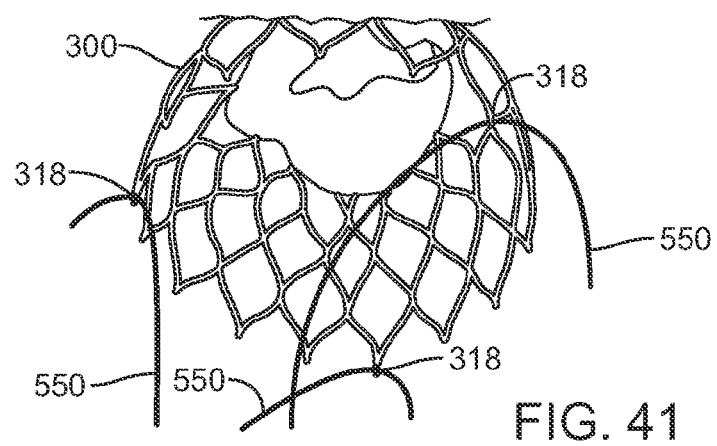
Figure 42:
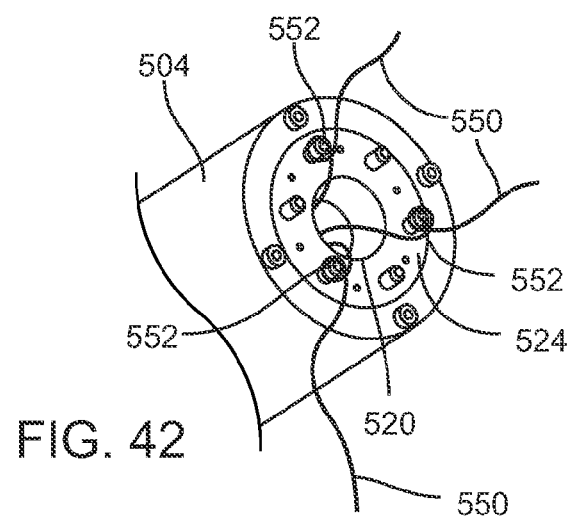
Figure 43:
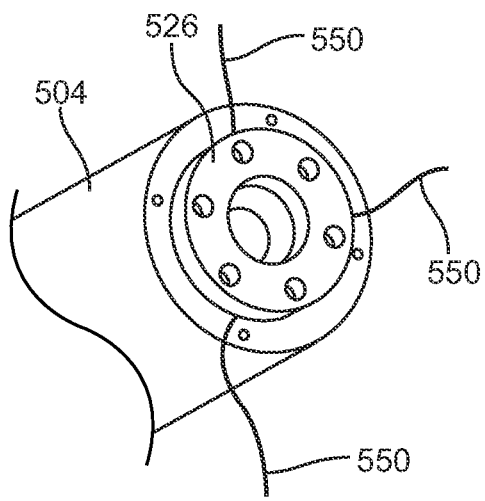
Figure 44:
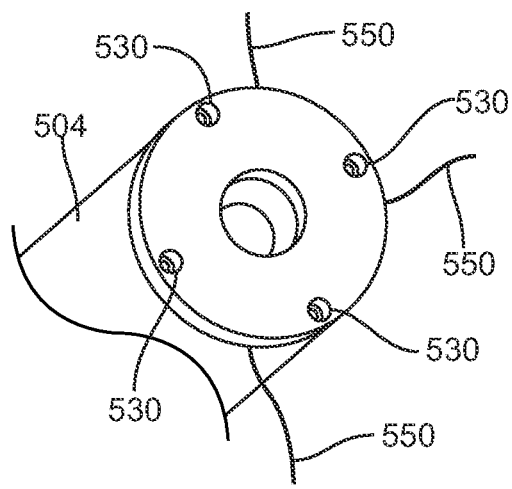
Figure 45:
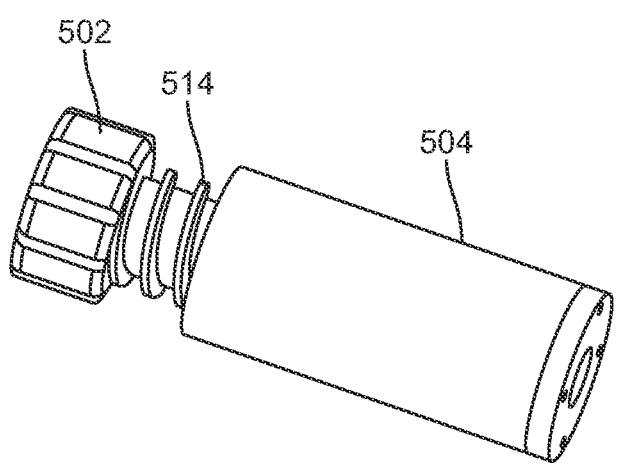

As illustrated in FIG. 41, one or more sutures 550 are threaded through loops 318 of valve 300. As illustrated in FIG. 42, the sutures 550 are then threaded out of opening 520 and wound around a plurality of pins 552 provided on rotating plate 524. In FIG. 43, locking plate 526 is positioned over rotating plate 524 so as to lock sutures 550 to the rotating plate 524. As shown in FIG. 44, lid 528 is positioned over the locking plate 526 so as to secure rotating plate 524 and locking plate 526 with respect to the housing 504 using fasteners 530. As illustrated in FIG. 45, housing portion 502 can be advanced away from housing portion 504 by rotating the housing portion 502 in a counter-clockwise direction relative to housing portion 504.

FIGS. 46 and 47 illustrate advancement of valve 300 to a compressed arrangement. In FIG. 46, valve 300 is loaded into funnel portion 502 and sutures 550 are threaded through the suture locking mechanism 522 as discussed above. In FIG. 47, housing portion 502 has been rotated in a counter-clockwise direction so as to advance the housing portion 502 away from housing portion 504. Sutures 550 thus pull valve 300 through the funnel segment 506 and into straight segment 508. Once valve 300 is exposed at open end 512 of housing portion 502, delivery system 30 can be attached to the valve 300 for final crimping. In an alternative embodiment, the delivery system 30 can be inserted into tool 500 and through valve 300 prior to crimping the valve 300. For example, delivery system 30 can be inserted into tool 500 in the step shown in FIG. 46.

Although the present disclosure has been described with reference to preferred embodiments, workers skilled in the art will recognize that changes can be made in form and detail without departing from the spirit and scope of the present disclosure.

What is claimed is:

1. A crimping tool for compressing a prosthesis to a compressed arrangement, comprising:
   a funnel segment;
   a suture locking mechanism;
   a plurality of sutures coupled to the prosthesis and the suture locking mechanism, the suture locking mechanism being operated to draw the prosthesis into the funnel segment and compress the prosthesis within the funnel segment, wherein the funnel segment is sized to engage support arms of the prosthesis and, upon transition to the compressed arrangement, the funnel segment operates to rotate the support arms with respect to a frame of the prosthesis so as to extend the support arms in a direction away from the frame.

2. The crimping tool of claim 1, wherein the suture locking mechanism includes a spring loaded pin for securing at least one of the plurality of sutures.

3. The crimping tool of claim 1, further comprising a spacer coupled to the funnel segment and including at least one channel for guiding loops of the prosthesis into the funnel segment.

4. The crimping tool of claim 1, further comprising a guide coupled to the funnel segment for guiding the sutures to the suture locking mechanism.

5. The crimping tool of claim 1, and further comprising a knob rotatable with respect to the funnel segment, the knob maintaining the suture locking mechanism.

6. The crimping tool of claim 1, further comprising a key configured to tension the sutures with the suture locking mechanism.

7. The crimping tool of claim 1, further comprising a suture loading tool configured to advance the plurality of sutures through the funnel segment.

8. The crimping tool of claim 1, further comprising a housing portion configured to rotatably engage the funnel segment such that rotation of the funnel segment causes the housing portion to move relative to the funnel segment.

9. The crimping tool of claim 1, wherein the suture locking mechanism comprises a plate maintaining a plurality of pins for securing the sutures.

10. The crimping tool of claim 1, further comprising a spacer coupled to the funnel segment, the spacer configured to engage support arms of the prosthesis and prolapse the support arms as the prosthesis transitions to the compressed arrangement.

11. A method for compressing a prosthesis from an expanded arrangement to a compressed arrangement, comprising:
    threading a plurality of sutures through the prosthesis;
    threading the plurality of sutures through a funnel segment and a straight segment;
    coupling the plurality of sutures to a suture locking mechanism; and
    rotating the suture locking mechanism to draw the prosthesis into the funnel segment and compress the prosthesis within the funnel segment, wherein the funnel segment is sized to engage support arms of the prosthesis and, upon transition to the compressed arrangement, the funnel segment operates to rotate the support arms with respect to a frame of the prosthesis so as to extend the support arms in a direction away from the frame.

12. The method of claim 11, wherein the suture locking mechanism includes a spring loaded pin for securing at least one of the plurality of sutures.

13. The method of claim 11, further comprising:
    providing a spacer coupled to the funnel segment for guiding loops of the prosthesis into the funnel segment.

14. The method of claim 11, further comprising:
    coupling a guide to the funnel segment to guide the sutures into the suture locking mechanism.

15. The method of claim 11, wherein a knob maintains the suture locking mechanism and the knob is rotatable with respect to the funnel segment.

16. The method of claim 11, further comprising:
    rotating a key coupled with the suture locking mechanism to tension the sutures.

17. The method of claim 11, further comprising:
    providing a housing portion configured to rotatably engage the funnel segment; and
    rotating the funnel segment to cause the housing portion to move relative to the funnel segment.

18. The method of claim 11, further comprising:
    securing the sutures to the suture locking mechanism with a plate maintaining a plurality of pins.

19. The method of claim 11, further comprising:
    coupling a spacer to the funnel segment, wherein the spacer engages support arms of the prosthesis and prolapses the support arms as the prosthesis transitions to the compressed arrangement.

20. A crimping tool for compressing a prosthesis to a compressed arrangement, comprising:
    a funnel segment;
    a suture locking mechanism;
    a plurality of sutures coupled to the prosthesis and the suture locking mechanism, the suture locking mechanism being operated to draw the prosthesis into the funnel segment and compress the prosthesis within the funnel segment, wherein the suture locking mechanism includes a spring loaded pin for securing at least one of the plurality of sutures.

21. A crimping tool for compressing a prosthesis to a compressed arrangement, comprising:
    a funnel segment;
    a suture locking mechanism;
    a plurality of sutures coupled to the prosthesis and the suture locking mechanism, the suture locking mechanism being operated to draw the prosthesis into the funnel segment and compress the prosthesis within the funnel segment, further comprising a spacer coupled to the funnel segment and including at least one channel for guiding loops of the prosthesis into the funnel segment.

22. A crimping tool for compressing a prosthesis to a compressed arrangement, comprising:
    a funnel segment;
    a suture locking mechanism;
    a plurality of sutures coupled to the prosthesis and the suture locking mechanism, the suture locking mechanism being operated to draw the prosthesis into the funnel segment and compress the prosthesis within the funnel segment; and
    a housing portion configured to rotatably engage the funnel segment such that rotation of the funnel segment causes the housing portion to move relative to the funnel segment.

* * * * *